(12) United States Patent
Pola

(10) Patent No.: US 6,552,070 B2
(45) Date of Patent: Apr. 22, 2003

(54) **HEALTH FOOD USEFUL FOR PREVENTING LIVER AND BILIARY DYSFUNCTIONS CONTAINING AN ALKANOYL L-CARNITINE AND *SILYBUM MARIANUM* EXTRACT**

(75) Inventor: Pietro Pola, Rome (IT)

(73) Assignee: Sigma-Tau HealthScience S.p.A., Rome (IT)

( * ) Notice: Subject to any disclaimer, the term of this patent is extended or adjusted under 35 U.S.C. 154(b) by 0 days.

(21) Appl. No.: 10/070,160

(22) PCT Filed: Jun. 26, 2001

(86) PCT No.: PCT/IT01/00333

§ 371 (c)(1),
(2), (4) Date: Mar. 4, 2002

(87) PCT Pub. No.: WO02/05831

PCT Pub. Date: Jan. 24, 2002

(65) Prior Publication Data

US 2002/0160082 A1 Oct. 31, 2002

(30) Foreign Application Priority Data

Jul. 14, 2000 (IT) ........................................ RM00A0387

(51) Int. Cl.⁷ ............................................. A61K 31/195

(52) U.S. Cl. ........................ 514/452; 514/456; 514/561; 514/893; 514/551; 424/439; 424/774; 424/778; 424/779; 426/655; 426/656

(58) Field of Search .................................. 514/452, 456, 514/551, 561, 893; 424/439, 774, 778, 779; 426/655, 656

(56) References Cited

U.S. PATENT DOCUMENTS

| | | | |
|---|---|---|---|
| 5,744,187 A | 4/1998 | Gaynor | 426/599 |
| 5,895,652 A | 4/1999 | Giampara | 424/195.1 |
| 5,904,924 A | 5/1999 | Gaynor et al. | 426/599 |

FOREIGN PATENT DOCUMENTS

| | | |
|---|---|---|
| DE | 197 44 459 A | 4/1999 |
| EP | 0 516 594 A | 12/1992 |
| WO | 99 43336 A | 9/1999 |

*Primary Examiner*—Frederick Krass
(74) *Attorney, Agent, or Firm*—Nixon & Vanderhye P.C.

(57) ABSTRACT

A health food/dietary supplement is disclosed, endowed with a protective action on liver function against exogenous and endogenous hepatoxic agents, the characterizing components of which are isovaleryl L-carnitine and/or propionyl L-carnitine and an extract of *Silybum marianum* (milk thistle) standardized to a least 70 percent by weight of silymarin.

14 Claims, No Drawings

HEALTH FOOD USEFUL FOR PREVENTING LIVER AND BILIARY DYSFUNCTIONS CONTAINING AN ALKANOYL L-CARNITINE AND *SILYBUM MARIANUM* EXTRACT

This application is the US national phase of international application PCT/IT01/00333 filed Jun. 26, 2001, which designated the US.

The present invention relates to a health food/dietary supplement containing as its characterising components an alkanoyl L-carnitine selected from the group comprising isovaleryl L-carnitine and propionyl L-carnitine or their pharmacologically acceptable salts or mixtures thereof and an extract of *Silybum marianum* (milk thistle) or its active components, among which most notably silymarin.

It has been found that the above-mentioned composition is extremely effective in exerting a potent protective action on liver function and integrity against lesions induced by various exogenous and endogenous hepatotoxic agents owing to the unexpected synergistic effect exerted by the interaction of its components.

Isovaleryl L-carnitine, a natural component of the carnitine pool, presents a specific activity at lysosomal level and on the cytosolic movements of calcium. It is therefore capable of intervening in proteolytic processes such as occur during intense and prolonged effort, and of protecting a number of organs such as the liver against the action of toxic substances.

Propionyl L-carnitine exerts an intense antioxidant effect and is particularly effective in improving the peripheral circulation and cardiac function.

In addition, muscular carnitine transferase possesses higher affinity for propionyl L-carnitine than for L-carnitine, and consequently propionyl L-carnitine possesses a higher degree of specificity for cardiac and skeletal muscle. Moreover, propionyl L-carnitine transferase by transporting the propionyl group increases the uptake of this component by the muscle cells, which may be particularly important for energy purposes, in that the propionate can be used by the mitochondria as an anapleurotic substrate and supply energy in the absence of oxygen.

The milk thistle is an indigenous plant cultivated for centuries in the Mediterranean region and South Western Europe and naturalised in most of Europe. It is also naturalised in North America, particularly California; in South America it is present from Uruguay to Chile and Ecuador; in Australia it runs wild; it is commonly found in abandoned fields, old pasture land and at the roadside.

The efficacy of the seeds of *Silybum marianum* or the milk thistle in preventing or treating various forms of liver or biliary dysfunction has been known for over two thousand years and is deeply rooted in popular tradition.

In 1968, silymarin, a flavanolignan complex was isolated from the plant. This consists mainly of three flavanolignans, silybin (silybinin), silychristin and silydianin. Other flavanolignans present are: dehydrosilybin, 3-deoxysilychristin, deoxysilydianin (silymonin), silyandrin, silybinome, silyermin and neosilyermin. Other constituents are apigeninin and silybonol; a fixed oil (16–18%), composed mainly of oleic acid and linoleic acid, in addition to myristic, palmitic and stearic acids.

In recent decades, few principles of vegetable origin have been studied as thoroughly as silymarin.

Its main activity is liver-protective and antioxidant. The liver-protective activity of silymarin has been demonstrated in numerous experimental models in which liver damage is induced by toxic substances, including carbon tetrachloride, galactosamine, thioacetamide, hepatotoxic cold-blooded frog virus, lanthanides and the toxins of *Amanita phalloides*, phalloidin and α-amanitin.

The liver-protective efficacy is based on various distinct mechanisms of action. Silymarin stimulates RNA polymerase A, increasing ribosomal protein synthesis and causing activation of the regenerative capacity of the liver through cell development. Silymarin interacts with the membranes of liver cells, blocking the binding sites and preventing intake of toxins, as demonstrated in rabbit liver microsomes and in mononuclear lipid layers. It is strongly antioxidative (free radical scavenger activity 10 times greater than that of Vitamin E), in that it blocks the release of malonyldialdehyde and antiperoxidative activity.

Clinical trials have suggested that preliminary treatments with silymarin inhibit the liver damage induced by alcohol, industrial chemicals and psychotrope drugs, accelerating the normalisation of impaired liver functions.

The patients receiving silymarin show a rapid improvement in elevated serum levels of glutamic-oxalacetic transaminase (GOT), glutamic-pyruvic transaminase (GPT) and γ-glutamyl transpeptidase (γ-GT).

The therapeutic activity of silymarin as a drug is extensively documented against liver damage, in chronic inflammation support treatment and in cirrhosis, including chronic hepatitis and fatty infiltration of the liver caused by alcohol and other chemicals. For the purposes of infusions, silbinin preparations are used for support treatment in cases of poisoning due to the toadstool Amanita.

In the herbalist or food product sector, the seeds of the plant or an extract of the seeds are used in tea, capsules, tablets and herb teas, mainly as a liver detoxifier.

The commercial preparations of milk thistle include ethanol extracts of seeds and/or fruits, pills or capsules (35–70 mg) standardised to 70% silymarin, in average daily doses of 200–400 mg.

It has now surprisingly been found that a composition containing as its characterising components a combination of:

(a) an alkanoyl L-carnitine selected from the group consisting of isovaleryl L-carnitine, propionyl L-carnitine or their pharmacologically acceptable salts or mixtures of the same; and (b) an extract of *Silybum marianum* standardised to at least 70% silymarin by weight, constitutes an effective health food/dietary supplement exerting a potent protective action on liver function and integrity against lesions induced by various exogenous and endogenous hepatotoxic agents owing to the potent and unexpected synergistic effect exerted by its components.

The dietary supplement described in this invention may additionally contain (c) a "carnitine" selected from the group comprising L-carnitine, acetyl L-carnitine, butyryl L-carnitine and valeryl L-carnitine, or their pharmacologically acceptable salts or mixtures thereof.

The weight-to-weight ratios of the above-mentioned components (a):(b):(c) range from 1:0.1:1 to 1:1:2.

The surprising synergistic effect which is achieved with the combination of "carnitines" (a term used to indicate collectively both L-carnitine and the alkanoyl L-carnitines), particularly isovaleryl L-carnitine and/or propionyl L-carnitine and the *Silybum marianum* extract, has been demonstrated by various pharmacological tests (some of which are described here below) chosen in such a way as to be strongly predictive of the practical use of this composition in the preventive, nutritional and dietetic fields.

Tests of Protection Against Toxic Effects Induced by Carbon Tetrachloride on Isolated Liver Cell Cultures In these tests, rat liver cells were isolated according to the method described by Segler (Segler P. O., Methods Cell. Biol. Chem., 264, 4747, 1989) and were used to determine the lipoperoxidative and toxic effects induced by $CCl_4$ (100 mg $L^{-1}$) measuring, in the supernatant liquid of the cell culture, the two markers, alanine-aminotransferase (AlaAT) and aspartate aminotransferase (AspAT) (Auto-biochemistry Assay System-Beckman 700—Encore-2), and malonaldehyde, as a peroxidation indicator, using the thiobarbituric acid method (Ohka W. H., Anal. Biochem., 95, 351, 1979).

The protective effect was then measured against $CCl_4$ toxicity by introducing into the liver cell cultures both isovaleryl L-carnitine (100 mg $L^{-1}$) and propionyl L-carnitine (100 mg $L^{-1}$) or silymarin (50 mg $L^{-1}$) or a combination of these products at the same doses. The cytology of the liver cells submitted to this treatment was also observed after fixation in formalin or glutaraldehyde, under both the optical and electron microscopes.

Tables 1 and 2 give the results of these tests which show that both isovaleryl L-carnitine and propionyl L-carnitine are capable of partly inhibiting the toxicity induced by $CCl_4$, whereas the protective effect exerted by silymarin is greater. Surprisingly effective is the protection induced by the combination of the above-mentioned alkanoyl L-carnitines and silymarin. In this case, in fact, the toxic and lipoperoxidative effects caused by $CCl_4$ on liver cell cultures are almost totally inhibited.

This significant and surprising protective effect was also detected in the cytological examination carried out on the liver cells, which revealed a reduction in the necrotic cells present in the culture, but was detectable above all at ultrastructural examination. In the control group ($CCl_4$), the cells showed heterochromatin abnormalities, disappearance of the mitochondrial crests in the mitochondria and a reduction in the number of ribosomes. In those cells which, in addition to $CCl_4$, were also exposed to the alkanoyl L-carnitines and silymarin, the cell membrane and the nucleus appeared unexpectedly intact and both the heterochromatins and mitochondria and the number of ribosomes appeared to be regular.

TABLE 1

Protection against $CCl_4$ toxicity on liver cell cultures
Concentration of AlaAT ($nmol.min^{-1}.L^{-1}$) in supernatant of liver cells exposed to $CCl_4$ (controls) together with isovaleryl L-carnitine (I), propionyl L-carnitine (P), and silymarin (S), alone or in combination

| Time (hours) | Controls | I | P | S | I + S | P + S |
|---|---|---|---|---|---|---|
| 4 | 26.8 ± 3.2 | 19.4 ± 2.4 | 22.3 ± 4.1 | 20.2 ± 3.1 | 10.4 ± 1.7 | 12.6 ± 1.8 |
| 8 | 28.6 ± 2.2 | 16.7 ± 3.1 | 18.4 ± 2.3 | 18.8 ± 2.7 | 8.5 ± 3.1 | 9.8 ± 2.1 |
| 16 | 32.4 ± 5.1 | 15.6 ± 2.7 | 16.6 ± 1.9 | 16.2 ± 1.7 | 5.2 ± 1.7 | 6.6 ± 2.7 |

TABLE 2

Concentration of AspAT ($nmol.min^{-1}.L^{-1}$) in supernatant of liver cells exposed to $CCl_4$ (controls) together with isovaleryl L-carnitine (I), propionyl L-carnitine (P), and silymarin (S), alone or in combination

| Time (hours) | Controls | I | P | S | I + S | P + S |
|---|---|---|---|---|---|---|
| 4 | 8.5 ± 0.6 | 6.9 ± 1.1 | 7.5 ± 0.9 | 6.4 ± 0.7 | 4.9 ± 0.8 | 5.1 ± 0.9 |
| 8 | 11.6 ± 0.1 | 6.2 ± 0.9 | 5.5 ± 1.2 | 5.1 ± 2.1 | 3.7 ± 0.5 | 4.0 ± 0.7 |
| 16 | 12.2 ± 1.1 | 5.5 ± 1.2 | 5.2 ± 1.4 | 4.9 ± 1.5 | 2.2 ± 0.8 | 2.5 ± 0.9 |

Tests of Protection Against Hepatotoxic Effects Induced by Galactosamine in the Rat In these tests, the protective activity of isovaleryl L-carnitine against galactosamine-induced liver intoxication was confirmed (Zezza F., Pharmacol. Res., 27, (Suppl. 1), 85, 1993). At the same time, a potent and surprising synergistic protective effect of the combination of isovaleryl L-carnitine and silymarin was detected against such intoxication, which presents characteristics similar to those of viral hepatitis.

In these tests the method adopted was that described by Reuter (Reuter W., Trends in the Therapy of Liver Diseases Proceeding, Ed. A. Bertelli, pp. 121, 1974, Karger Basel 1975).

Rats weighing approximately 250 g received daily oral administrations for two days consecutively of 200 mg/kg of isovaleryl L-carnitine or 200 mg/kg of propionyl L-carnitine or 100 mg/kg of silymarin or a combination of these compounds at the same doses. After 24 hours, the same rats were administered 400 mg/kg i.p. of galactosamine. After a further 24 hours, blood samples taken from the animals were used to determine both glutamic-oxalacetic transferase (GOT) and the bilirubin present in plasma, according to the method described by Keppler (Keppler D., Exp. Mol. Pathol, 9, 279, 1968). Both the enzyme activity and bilirubin were reduced by the administration of propionyl L-carnitine or, to a greater extent, by isovaleryl L-carnitine and silymarin, but returned to levels close to normal with the administration of the alkanoyl L-carnitine/silymarin combination.

TABLE 3

Galactosamine intoxication tests

| Treatment | GOT | GluDH | Bilirubin |
|---|---|---|---|
| Controls | 25 ± 4 | 4.5 ± 0.4 | 0.12 ± 0.01 |
| Galactosamine | 750 ± 68 | 595 ± 51 | 1.08 ± 0.51 |
| Isovaleryl L-carnitine | 215 ± 30.5 | 64 ± 6.8 | 0.15 ± 0.04 |

TABLE 3-continued

Galactosamine intoxication tests

| Treatment | GOT | GluDH | Bilirubin |
|---|---|---|---|
| Silymarin | 125 ± 15.3 | 71 ± 5.5 | 0.14 ± 0.02 |
| Isovaleryl L-carnitine + silymarin | 34.4 ± 5.2 | 5.8 ± 0.6 | 0.11 ± 0.03 |
| Propionyl L-carnitine + silymarin | 45.7 ± 4.4 | 6.5 ± 0.7 | 0.12 ± 0.05 |

Some non-limiting examples of combination compositions according to the present invention are given hereinbelow:

| | | |
|---|---|---|
| 1) | Propionyl L-carnitine | 500 mg |
| | Extract of milk thistle containing flavanolignans expressed as silymarin | 200 mg |
| 2) | Isovaleryl L-carnitine | 500 mg |
| | Extract of milk thistle containing flavanolignans expressed as silymarin | 200 mg |
| 3) | Isovaleryl L-carnitine | 150 mg |
| | Propionyl L-carnitine | 150 mg |
| | Acetyl L-carnitine | 150 mg |
| | Extract of milk thistle containing flavanolignans expressed as silymarin | 200 mg |
| 4) | Isovaleryl L-carnitine | 400 mg |
| | Extract of milk thistle containing flavanolignans expressed as silymarin | 100 mg |
| | Choline | 50 mg |
| | Arginine | 50 mg |
| | Lysine | 50 mg |
| | Ornithine | 25 mg |
| | Inositol | 50 mg |
| | Methionine | 25 mg |
| 5) | Isovaleryl L-carnitine | 400 mg |
| | Extract of milk thistle containing flavanolignans expressed as silymarin | 100 mg |
| | Extract of Cynara scolimus (artichoke) expressed as cynarine | 25 mg |
| | Vit. C | 50 mg |
| | Vit. E | 5 mg |
| | Vit. PP | 25 mg |
| | Choline | 50 mg |
| | Coenzime $Q_{10}$ | 25 mg |
| | Selenomethionine | 50 μg |

What is meant by a pharmacologically acceptable salt of the various aforesaid carnitines mentioned in the present specification is, in addition to the respective "inner salts", any salt of these with an acid which does not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

Among these salts, isovaleryl L-carnitine acid fumarate (U.S. Pat. No. 5,227,518) is particularly preferred.

A list of FDA-approved pharmacologically acceptable acids is given in Int. J. Pharm., 33, 1986, 201–217, the latter publication being incorporated in the present specification by reference.

The supplement of the invention may further comprise vitamins, coenzymes, mineral substances, aminoacids and antioxidants. The supplement may be manufactured in the form of tablets, lozenges, capsules, pills, granulates, syrups, herb teas, vials or drops.

What is claimed is:

1. A food/dietary supplement for protecting liver function which comprises a synergistic combination of the following ingredients:

(a) an alkanoyl L-carnitine selected from the group consisting of isovaleryl L-carnitine, propionyl L-carnitine and pharmacologically acceptable salts thereof or mixtures thereof; and (b) an extract of Silybum marianum standardized to at least 70% by weight of silymarin.

2. The supplement of claim 1, further comprising:

(c) a carnitine selected from the group consisting of L-carnitine, acetyl L-carnitine, butyryl L-carnitine and valeryl L-carnitine and pharmacologically acceptable salts or mixtures thereof.

3. The supplement of claim 1 which further comprises vitamins, sugars, coenzymes, minerals, aminoacids, peptides and antioxidants.

4. The supplement of claim 1 wherein the pharmacologicallly acceptable salt is selected from the group consisting of: chloride; bromide; iodide; aspartate, citrate, tartrate; phosphate, fumarate, glycerophosphate; glucose phosphate; lactate; maleate; mucate; orotate; oxalate; sulphate, trichloroacetate; trifluoroacetate and methane sulphonate.

5. The supplement of claim 1 having protective action on liver function and integrity against lesions induced by exogenous and endogenous hepatotoxic agents.

6. The supplement of claim 1 manufactured in solid or liquid form.

7. The supplement of claim 1 in the form of tablets, capsules, lozenges, pills, granulates, syrups, herb teas, vials or drops.

8. The supplement of claim 2 wherein the weight ratio of components (a):(b):(c) ranges from 1:0.1:1 to 1:1:2.

9. The supplement of claim 8, in unit dosage form, comprising:

| | |
|---|---|
| Propionyl L-carnitine | 500 mg |
| Extract of milk thistle containing flavanolignans expressed as silymarin. | 200 mg |

10. The supplement of claim 8, in unit dosage form, comprising:

| | |
|---|---|
| Isovaleryl L-carnitine | 500 mg |
| Extract of milk thistle containing flavanolignans expressed as silymarin. | 200 mg |

11. The supplement of claim 8, in unit dosage form, comprising:

| | |
|---|---|
| Isovaleryl L-carnitine | 150 mg |
| Propionyl L-carnitine | 150 mg |
| Acetyl L-carnitine | 150 mg |
| Extract of milk thistle containing flavanolignans expressed as silymarin. | 200 mg |

12. The supplement of claim 8, in unit dosage form, comprising:

| | |
|---|---|
| Isovaleryl L-carnitine | 400 mg |
| Extract of milk thistle containing flavanolignans expressed as silymarin | 100 mg |
| Choline | 50 mg |
| Arginine | 50 mg |
| Lysine | 50 mg |
| Ornithine | 25 mg |
| Inositol | 50 mg |
| Methionine | 25 mg. |

13. The supplement of claim 8, in unit dosage form, comprising:

| | |
|---|---|
| Isovaleryl L-carnitine | 400 mg |
| Extract of milk thistle containing flavanolignans expressed as silymarin | 100 mg |
| Extract of *Cynara scolimus* (artichoke) expressed as cynarine | 25 mg |
| Vit. C | 50 mg |
| Vit. E | 5 mg |
| Vit. PP | 25 mg |
| Choline | 50 mg |
| Coenzime $Q_{10}$ | 25 mg |
| Selenomethionine | 50 μg. |

14. A method for preventing damage induced by exposure to exogenous and endogenous hepatotoxic agents and for protecting liver function and integrity which comprises administering to an individual in need thereof a synergistic combination consisting of the following ingredients:

(a) an alkanoyl L-carnitine selected from the group consisting of isovaleryl L-carnitine, propionyl L-carnitine and pharmacologically acceptable salts thereof or mixtures thereof; and (b) an extract of *Silybum marianum* standardized to at least 70% by weight of silymarin.

* * * * *